(12) United States Patent
Mellman et al.

(10) Patent No.: US 8,889,117 B2
(45) Date of Patent: *Nov. 18, 2014

(54) MODULAR NANOPARTICLES FOR ADAPTABLE VACCINES

(75) Inventors: Ira S. Mellman, San Francisco, CA (US); Tarek M. Fahmy, New Haven, CT (US); William Mark Saltzman, New Haven, CT (US); Michael J. Caplan, Woodbridge, CT (US)

(73) Assignee: Yale University, New Haven, CT (US)

( * ) Notice: Subject to any disclaimer, the term of this patent is extended or adjusted under 35 U.S.C. 154(b) by 99 days.

This patent is subject to a terminal disclaimer.

(21) Appl. No.: 12/527,143

(22) PCT Filed: Feb. 15, 2008

(86) PCT No.: PCT/US2008/054086
§ 371 (c)(1),
(2), (4) Date: Aug. 13, 2009

(87) PCT Pub. No.: WO2008/115641
PCT Pub. Date: Sep. 25, 2008

(65) Prior Publication Data
US 2010/0104503 A1    Apr. 29, 2010

Related U.S. Application Data

(60) Provisional application No. 60/890,133, filed on Feb. 15, 2007, provisional application No. 61/000,016, filed on Oct. 23, 2007.

(51) Int. Cl.
| | |
|---|---|
| *A61K 39/00* | (2006.01) |
| *C07K 14/00* | (2006.01) |
| *A61K 47/48* | (2006.01) |
| *B82Y 5/00* | (2011.01) |

(52) U.S. Cl.
CPC ............ *A61K 39/00* (2013.01); *A61K 47/48561* (2013.01); *A61K 47/48892* (2013.01); *B82Y 5/00* (2013.01); *A61K 47/48915* (2013.01)
USPC ........................................................ 424/85.1

(58) Field of Classification Search
None
See application file for complete search history.

(56) References Cited

U.S. PATENT DOCUMENTS

| | | | |
|---|---|---|---|
| 6,544,543 B1 | 4/2003 | Mandrusov | |
| 7,534,448 B2 * | 5/2009 | Saltzman et al. | ............. 424/417 |
| 2001/0031262 A1 * | 10/2001 | Caplan et al. | ............. 424/178.1 |
| 2002/0044959 A1 | 4/2002 | Goetz | |
| 2006/0002971 A1 | 1/2006 | Saltzman | |
| 2010/0284965 A1 | 11/2010 | Fahmy | |

FOREIGN PATENT DOCUMENTS

| | | |
|---|---|---|
| WO | 9503357 | 2/1995 |
| WO | 02076441 | 10/2002 |
| WO | 03087021 | 10/2003 |
| WO | 2005021730 | 3/2010 |

OTHER PUBLICATIONS

Cannizzaro, et al., "A novel biotinylated degradable polymer for cell-interactive applications", Biotech Bioeng., 58(5):529-35 (1998).

* cited by examiner

*Primary Examiner* — Yunsoo Kim
(74) *Attorney, Agent, or Firm* — Pabst Patent Group LLP

(57) ABSTRACT

Modular nanoparticle vaccine compositions and methods of making and using the same have been developed. Modular nanoparticle vaccine compositions comprise an antigen encapsulated in a polymeric particle and adaptor elements which modularly couple functional elements to the particle. The modular design of these vaccine compositions, which involves flexible addition and subtraction of antigen, adjuvant, immune potentiators, molecular recognition and transport mediation elements, as well as intracellular uptake mediators, allows for exquisite control over variables that are important in optimizing an effective vaccine delivery system.

18 Claims, 3 Drawing Sheets

MODULAR NANOPARTICLES FOR ADAPTABLE VACCINES

CROSS-REFERENCE TO RELATED APPLICATIONS

This application is a filing under 35 U.S.C. 371 of PCT/US2008/054086 filed with the U.S. Receiving Office of the Patent Cooperation Treaty on Feb. 15, 2008, which claims priority to and benefit of U.S. Provisional Patent Application No. 60/890,133 filed on Feb. 15, 2007 and U.S. Provisional Patent Application No. 61/000,016 filed on Oct. 23, 2007, and where permissible is incorporated by reference in its entirety.

GOVERNMENT SUPPORT

The United States government has certain rights in this invention by virtue of National Science Foundation Grant Number 0609326 to Tarek Fahmy.

FIELD OF THE INVENTION

The present disclosure generally relates to the field of modular nanoscale vaccine compositions and methods of making and using these compositions.

BACKGROUND OF THE INVENTION

Preventative vaccines have eliminated smallpox and nearly eliminated polio, two of the worst global infectious diseases. By contrast vaccines for many other infectious diseases, such as malaria and HIV, which involve intracellular pathogens, are poorly developed or simply unavailable (Singh and O'Hagan, *Pharm. Res.*, 19(6):715-28 (2002); O'Hagan and Valiante, *Nat. Rev. Drug Discov.*, 2(9):727-35 (2003)). The lack of such vaccines results in two million unnecessary deaths each year in many parts of the world (WHO, State of the Art New Vaccines (2003)).

Several key variables are needed in the design of effective vaccines (Pashine, et al., *Nat. Med.*, 11(4 Suppl):S63-8 (2005), Bramwell and Perrie, *Drug Discovery Today*, 10(22):1527-34 (2005)). The first variable is the form of the antigen itself, which can be whole inactivated or attenuated organisms, purified proteins and peptides, or DNA encoded antigens. Human pathogens are continually emerging and changing (e.g. SARS, avian flu) meaning that new potential immunogens are constantly appearing. Thus, there is a clear need to design vaccine systems that can rapidly and efficiently test the efficacy of vaccines involving new antigens (Bramwell, et al., *Adv. Drug Deliv Rev.* 57(9):1247-65 (2005)). Large scale and safe production of stable vaccine products typically involves the purification of natural or recombinant forms of antigenic subunits. Once purified, however, individual antigens often become less immunogenic compared to whole pathogens or crude extracts, necessitating a means to amplify the immune response against the purified subunit antigen. Thus, a second necessary component of a vaccine involves providing an adjuvant or other means for potentiating or stimulating both the innate and adaptive arms of the immune system to the antigen subunit (Pashine, et al., *Nat. Med.*, 11(4 Suppl):S63-8 (2005), Bramwell and Perrie, *Drug Discovery Today*, 10(22):1527-34 (2005)).

Immune potentiators may include bacterial products, toxins or other molecules that augment specific immunity. Potentiators have various benefits, but also attendant risks such as triggering deleterious inflammatory responses. To affect optimal stimulation to a given antigen, a formulation is needed that delivers the correct amount of antigen in a repetitive or sustained fashion, to the appropriate immune cells and to the appropriate compartments within those cells. Thus, a designed delivery vehicle (adjuvant) should target the vaccine antigen and facilitate delivery of both antigen and immune potentiating molecules selectively to target cells of the immune system. This is highly reminiscent of the strategy taken by viruses that inactivate specific components of the immune system during infection. Traditional methods for increasing the effectiveness of vaccines have focused on co-administration of adjuvants or use of a delivery system.

While the adjuvant role is critical, there are obvious risks, costs and limitations associated with this traditional approach. For example, currently available adjuvants, represented predominately by colloidal alum (aluminum sulfate or aluminum hydroxide) or montanide polymers, have a limited capacity to adsorb many antigens and have greatly limited immunostimulatory properties (Gupta and Siber, *Vaccine*, 13(14):1263-76 (1995); Lindblad, *Vaccine*, 22(27-28):3658-68 (2004)). There are also risks associated with using live attenuated vaccines and allergic side effects associated with aluminum salts (Lindblad, *Vaccine*, 22(27-28):3658-68 (2004); Gupta, et al., *Vaccine*, 11(3):293-306 (1993)). Additionally, because of the historical emphasis on eliciting humoral immune responses, most adjuvants are optimized for effective induction of high antibody serum titers, but are ineffective at eliciting a strong cellular, T cell-mediated immune response or strong mucosal immune response. T cell responses are essential for inducing lasting viral immunity (or immune responses to cancer); mucosal immunity is essential for protective responses to cellular and viral pathogens that are transmitted through mucosal surfaces (e.g. human immunodeficiency virus, HIV; herpes simplex virus, HSV; enteric pathogens). These factors, coupled with the difficulties of manufacture, storage, and transport have together greatly limited the utility of current approaches in the clinic and in the field (O'Hagan and Valiante, *Nat. Rev. Drug Discov.*, 2(9):727-35 (2003); Sigh and Srivastava, Curr. HIV Res., 1(3):309-20 (2003), Singh and O'Hagan, *Nat. Biotechnol.*, 17(11):1075-81 (1999)).

Thus, in addition to economic factors, as outlined above, there are a number of significant scientific challenges that have limited the development of vaccines for deadly diseases. First, few if any approaches are available that efficiently prime cell-mediated immunity by direct intracellular delivery of an antigen. Second, 'tunable' adjuvants, that is, adjuvants that can be engineered to optimize the magnitude and direction of an immune response (Jiang, et al., *Adv. Drug Deliv. Rev.*, 57(3):391-410 (2005); Sesardic and Dobbelaer, *Vaccine*, 22(19):2452-6 (2004)) have not been developed. Third, alternatives are not available for the general requirement for parenteral (i.e. subcutaneous or intramuscular injection) administration of vaccines, a situation that has made it difficult to deploy vaccines in underdeveloped countries where medical support systems, resources, and cold-storage are limited. Finally, there is no general approach to designing oral vaccines targeted to both systemic and mucosal immunity. This would be highly advantageous since oral vaccines are significantly less expensive to administer and transport. Thus, there is a critical need for safe and stable vaccine systems that would address all these factors (Friede and Aguado, *Adv. Drug Deliv. Rev.*, 57(3):325-31 (2005); Storni, et al., *Adv. Drug Deliv. Rev.*, 57(3):333-55 (2005); Gupta, et al., *Adv. Drug Deliv. Rev.*, 32(3):225-246 (1998); Aguado and Lambert, *Immunobiology*, 184(2-3):113-25 (1992)).

It is therefore an object of the invention to provide stable vaccine formulations which can be orally administered.

It is another object of the invention to provide modular nanoparticulate vaccine compositions which provide for flexible addition and subtraction of elements.

It is still another object of the invention to provide means for modulating an immune response, either to increase or decrease the response, or bias the response to a humoral or cellular immune response.

It is a further object of the invention to provide methods for making and using such modular nanoparticulate vaccine compositions.

SUMMARY OF THE INVENTION

Modular nanoparticle vaccine compositions and methods of making and using them have been developed. The modular design of these nanoparticle vaccine compositions, which involves flexible addition and subtraction of antigen, adjuvant and/or immune potentiators, molecular recognition factors, and transport mediation elements, as well as intracellular uptake mediators, allows for exquisite control over many of the variables that are important for optimizing an effective vaccine delivery system. A key feature of these nanodevices is their ability to be selectively targeted to those cells of the immune system that are most closely associated with producing the desired immunological response for a given vaccine. This is accomplished by encapsulating any vaccine antigen within the nanoparticles, together with the activators of the desired immune activity. The nanoparticle surface is then modified by the direct or indirect coupling of targeting molecules, such as antibodies, that will guide the entire nanodevice to specific cell types (such as dendritic cells) associated with stimulating or suppressing immune responses. The targeted particles are constructed to bind to the intended cell type, to be internalized by endocytosis, and then to dissociate, thereby releasing the encapsulated antigen and immune activators (adjuvants). The modular nature of the nanodevice enables rapid production and the ability to modify the nanoparticle surface with any of a variety of targeting molecules, enabling targeting to different cell types, such as various dendritic cell subsets, epithelial cells, or macrophages. The adjuvant composition can also be easily altered to enable the systematic assessment of optimal targeting and composition for any desired application. The nanodevices can be easily characterized biochemically using conventional ELISA and flow cytometry assays, and by in vitro or in vivo assays for antigen presentation and immune stimulation.

Modular nanoparticle vaccine compositions include an antigen incorporated or encapsulated in a polymeric nanoparticle. Antigens may be viral, bacterial, parasitic, allergen, toxoid, tumor-specific or tumor-associated antigens, which can be one or more proteins, carbohydrates, lipids, nucleic acids, or combinations thereof. The nanoparticle further includes adaptor elements which modularly couple functional elements to the particle. In the preferred embodiment, the adaptor elements are fatty acids, hydrophobic or amphipathic peptides, or hydrophobic polymers. Adaptor elements can be conjugated to affinity tags, which allow for modular assembly and disassembly of functional elements which are conjugated to complementary affinity tags to the nanoparticle. Functional elements impart useful functions to the nanoparticle compositions. Functional elements may include, for example, dendritic cell targeting molecules, epithelial cell targeting molecules, pH-sensitive or non-pH-sensitive molecules which protect the vaccine composition from hydrolysis and degradation in low pH environments, and endosome-disrupting agents. Nanoparticle vaccine compositions may further include adjuvants, contrast agents and other markers and pharmaceutically acceptable excipients.

The ability to target exogenous antigens to internalizing surface molecules on antigen-presenting cells facilitates the uptake of antigens and their presentation to lymphocytes and thus overcomes a major rate-limiting step in vaccination. The ability to target vaccine compositions to epithelial cells in the digestive tract greatly facilitates the ability of a vaccine to induce mucosal and systemic immunity when administered orally. Molecules which protect the vaccine composition from hydrolysis and degradation in low pH environments also enhance the efficacy of vaccines administered orally. Endosome-disrupting agents function to cause limited disruption of endosome-lysosome membranes during antigen uptake by antigen-presenting cells. This allows the antigen to enter the cytoplasm and be presented on MHC class I molecules on the surface of antigen-presenting cells in a process known as cross-presentation. Cross-presentation allows for the activation of cytotoxic CD8 positive T cells which greatly enhances the effectiveness of vaccination. The modular nanoparticulate vaccine compositions offer several advantages over other vaccines: 1) targeting of different cells, thereby enabling optimal selection of different tissue and priming for antigen presentation; 2) delivery of a wide variety of antigens of clinical importance; and 3) rapid assembly of different combinations of protective, recognition and antigen modules to affect a broad-spectrum potent vaccine response.

DETAILED DESCRIPTION OF THE INVENTION

Figure 1:
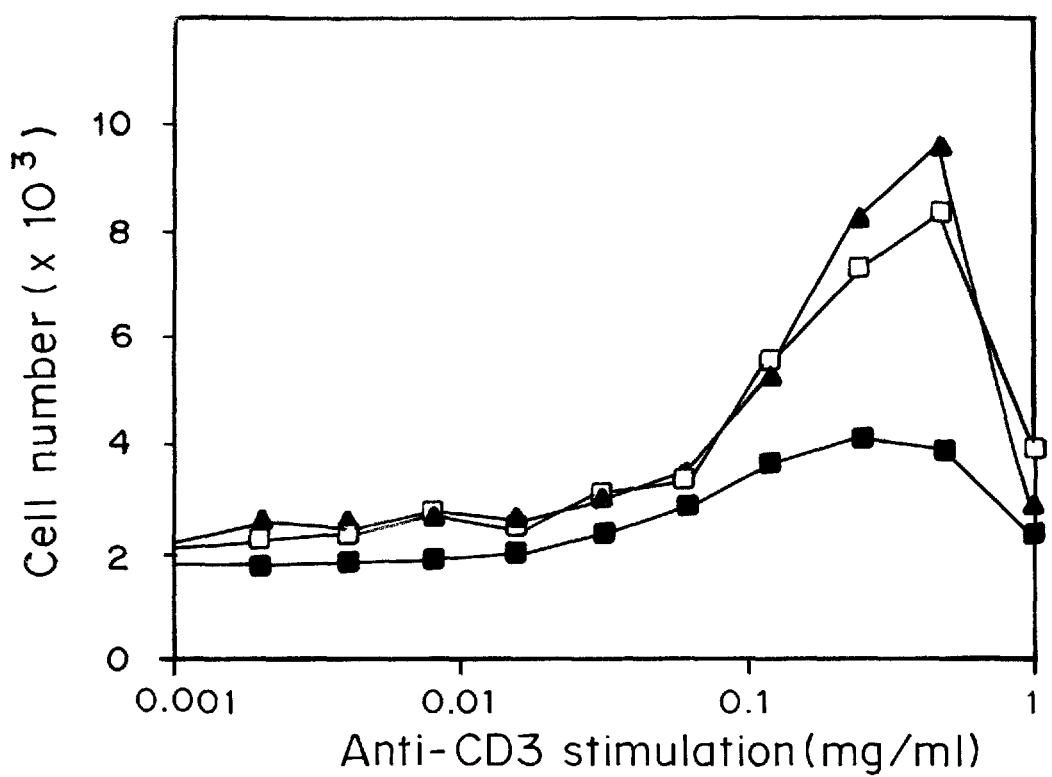
FIG. 1 is a graph demonstrating inhibition of CD3-stimulated T-cell proliferation (number of cells) when T-cells are exposed to doxorubicin-loaded particles modified with an antibody (-■-) that recognizes T-cells at the indicated concentration (mg/ml). Controls are doxorubicin-loaded nanoparticles without antibody (-□-) and blank nanoparticles (-▲-).

A solution to the vaccine problem requires a systematic approach that addresses each of the design challenges discussed above. Viruses and pathogens that elicit or subvert immune responses are, in essence, small particles endowed with the ability to interact with or avoid cells of the immune system in a variety of ways. The vaccines described herein are based on an approach in which nanoscale modules are assembled into units that are optimized for stimulating immune responses to a specific pathogen. The principles of nanoassembly is used to design safe vaccine vectors that are highly optimized to protect against disease and provide new treatment options for disorders such as asthma, allergy, and cancer.

I. Definitions

"Affinity tags" are defined herein as molecular species which form highly specific, non-covalent, physiochemical interactions with defined binding partners. Affinity tags which form highly specific, non-covalent, physiochemical interactions with one another are defined herein as "complementary".

"Adaptor elements" are defined herein as molecular entities which associate with polymeric nanoparticles and provide substrates that facilitate the modular assembly and disassembly of functional elements onto the nanoparticle. Adaptor elements can be conjugated to affinity tags. Affinity tags allow for flexible assembly and disassembly of functional elements which are conjugated to affinity tags that form highly specific, noncovalent, physiochemical interactions with affinity tags conjugated to adaptor elements. Adaptor elements can also be covalently coupled to functional elements in the absence of affinity tags.

"Functional elements" are defined herein as molecular entities which associate with nanoparticles and impart a particular function to the nanoparticle. Functional elements can associate with nanoparticles through adaptor elements, or through direct association with the nanoparticle surface. Functional elements can be conjugated to affinity tags which form highly specific, noncovalent, physiochemical interactions with complementary affinity tags conjugated to adaptor elements. Thus, functional elements can be coupled to adaptor elements noncovalently through affinity tags. Alternatively, functional elements can be covalently coupled to adaptor elements in the absence of affinity tags. Functional elements can also be covalently or noncovalently associated with the surface of nanoparticles without the use of adaptor elements.

An "antigen" is defined herein as a molecule which contains one or more epitopes that will stimulate a hoses immune system to make a cellular antigen-specific immune response, and/or a humoral antibody response. Antigens can be peptides, proteins, polysaccharides, saccharides, lipids, nucleic acids, and combinations thereof. The antigen can be derived from a virus, bacterium, parasite, plant, protozoan, fungus, tissue or transformed cell such as a cancer or leukemic cell and can be a whole cell or immunogenic component thereof, e.g., cell wall components. An antigen may be an oligonucleotide or polynucleotide which expresses an antigen. Antigens can be natural or synthetic antigens, for example, haptens, polyepitopes, flanking epitopes, and other recombinant or synthetically derived antigens (Bergmann, et al., *Eur. J. Immunol.*, 23:2777-2781 (1993); Bergmann, et al., *J. Immunol.*, 157:3242-3249 (1996); Suhrbier, *Immunol. and Cell Biol.*, 75:402-408 (1997).

A "tumor-specific antigen" is defined herein as an antigen that is unique to tumor cells and does not occur in or on other cells in the body.

A "tumor-associated antigen" is defined herein as an antigen that is not unique to a tumor cell and is also expressed in or on a normal cell under conditions that fail to induce an immune response to the antigen.

An "adjuvant" is defined herein as a substance increasing the immune response to other antigens when administered with other antigens. Adjuvants are also referred to herein as "immune potentiators" and "immune modulators".

"Antigen-presenting cells" are defined herein as highly specialized cells that can process antigens and display their peptide fragments on the cell surface together with molecules required for lymphocyte activation. The major antigen-presenting cells for T cells are dendritic cells, macrophages and B cells. The major antigen-presenting cells for B cells are follicular dendritic cells.

"Cross-presentation" is defined herein as the ability of antigen-presenting cells to take up, process and present extracellular antigens with MHC class I molecules to CD8 T cells (cytotoxic T cells). This process induces cellular immunity against most tumors and against viruses that do not infect antigen-presenting cells. Cross-presentation is also required for induction of cytotoxic immunity by vaccination with protein antigens, for example in tumor vaccination.

An "endosome-disrupting agent" is defined herein as any agent which causes disruption of endosomal membranes during endocytosis. Endosome-disrupting agents facilitate the transit of extracellular antigens into the cytoplasm of antigen-presenting cells, where they can be imported into the endoplasmic reticulum and processed for cross-presentation on MHC class I molecules at the cell surface.

"Dendritic cell targeting molecules" are defined herein as molecules that target and facilitate endocytosis of nanoparticles by dendritic cells. Dendritic cell targeting molecules may be directly coupled to nanoparticles, or may be coupled to nanoparticles through adaptor elements. In a preferred embodiment the dendritic cell targeting molecules are functionally coupled to adaptor elements.

"Epithelial cell targeting molecules" are defined herein as molecules that target the nanoparticles to epithelium and mediate transcytosis to underlying antigen-presenting cells. Epithelial cell targeting molecules may be directly coupled to nanoparticles, or may be coupled to nanoparticles through adaptor elements. In a preferred embodiment the epithelial cell targeting molecules are functionally coupled to adaptor elements.

As used herein, the phrase that a molecule "specifically binds" to a target refers to a binding reaction which is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity. Specific binding between two entities means an affinity of at least $10^6$, $10^7$, $10^8$, $10^9$, or $10^{10}$ $M^{-1}$. Affinities greater than $10^8$ $M^{-1}$ are preferred.

As used herein, the terms "antibody" or "immunoglobulin" are used to include intact antibodies and binding fragments thereof. Typically, fragments compete with the intact antibody from which they were derived for specific binding to an antigen fragment including separate heavy chains, light chains Fab, Fab' F(ab')2, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992).

As used herein, the terms "epitope" or "antigenic determinant" refer to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids, in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., J. Inf. Dis. 170, 1110-19 (1994)), by antigen-dependent killing (cytotoxic T lymphocyte assay, Tigges et al., J. Immunol. 156, 3901-3910) or by cytokine secretion.

As used herein, the terms "immunologic", "immunological" or "immune" response is the development of a humoral (antibody mediated) and/or a cellular (mediated by antigen-specific T cells or their secretion products) response directed against an antigen. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific CD4$^+$ T helper cells and/or CD8$^+$ cytotoxic T cells. The response may also involve activation of monocytes, macrophages, NK cells, basophils, dendritic cells, astrocytes, microglia cells, eosinophils or other components of innate immunity. The presence of a cell-mediated immunological response can be determined by proliferation assays (CD4$^+$ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

As used herein, a "costimulatory polypeptide" or a "costimulatory molecule" is a polypeptide that, upon interaction with a cell-surface molecule on T cells, enhances T cell responses, enhances proliferation of T cells, enhances production and/or secretion of cytokines by T cells, stimulates differentiation and effector functions of T cells or promotes survival of T cells relative to T cells not contacted with a costimulatory peptide.

The terms "individual", "host", "subject", and "patient" are used interchangeably herein, and refer to a mammal, including, but not limited to, murines, simians, humans, mammalian farm animals, mammalian sport animals, and mammalian pets.

II. Modular Nanoparticulate Vaccine Compositions

Modular nanodevice vaccine systems are constructed from nanoparticles. The modular design of these nanoparticle vaccine compositions, which involves flexible addition and subtraction of antigen, adjuvant, immune potentiators, molecular recognition, and/or transport mediation elements, as well as intracellular uptake mediators, allows for exquisite control over many of the variables that are important for optimizing an effective vaccine delivery system.

A. Polymeric Nanoparticles

As used herein, nanoparticles generally refers to particles in the range of between 500 nm to less than 0.5 nm, preferably having a diameter that is between 50 and 500 nm.

The polymer that forms the core of the modular vaccine nanoparticle may be any biodegradable or non-biodegradable synthetic or natural polymer. In a preferred embodiment, the polymer is a biodegradable polymer. These systems have several features that make them ideal materials for the fabrication of a vaccine nanodevice: 1) control over the size range of fabrication, down to 100 nm or less, an important feature for passing through biological barriers; 2) reproducible biodegradability without the addition of enzymes or cofactors; 3) capability for sustained release of an encapsulated, protected antigen over a period in the range of days to months by varying factors such as the monomer ratios or polymer size, for example, poly(lactic acid) (PLA) to poly(glycolic acid) (PGA) copolymer ratios, potentially abrogating the booster requirement (Gupta, et al., *Adv. Drug Deliv. Rev.*, 32(3):225-246 (1998); Kohn, et al., *J. Immunol. Methods*, 95(1):31-8 (1986); Langer, et al., *Adv. Drug Deliv. Rev.*, 28(1):97-119 (1997); Jiang, et al., *Adv. Drug Deliv. Rev.*, 57(3):391-410)), well-understood fabrication methodologies that offer flexibility over the range of parameters that can be used for fabrication, including choices of the polymer material, solvent, stabilizer, and scale of production; and 5) control over surface properties facilitating the introduction of modular functionalities into the surface.

Examples of preferred biodegradable polymers include synthetic polymers that degrade by hydrolysis such as poly (hydroxy acids), such as polymers and copolymers of lactic acid and glycolic acid, polyanhydrides, poly(ortho)esters, polyesters, polyurethanes, poly(butic acid), poly(valeric acid), poly(caprolactone), poly(hydroxyalkanoates), and poly(lactide-co-caprolactone).

Preferred natural polymers include alginate and other polysaccharides, collagen, albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

In some embodiments, non-biodegradable polymers can be used, especially hydrophobic polymers. Examples of preferred non-biodegradable polymers include ethylene vinyl acetate, poly(meth) acrylic acid, copolymers of maleic anhydride with other unsaturated polymerizable monomers, poly (butadiene maleic anhydride), polyamides, copolymers and mixtures thereof, and dextran, cellulose and derivatives thereof.

Other suitable biodegradable and non-biodegradable polymers include, but are not limited to, polyanhydrides, polyamides, polycarbonates, polyalkylenes, polyalkylene oxides such as polyethylene glycol, polyalkylene terepthalates such as poly(ethylene terephthalate), polyvinyl alcohols, polyvinyl ethers, polyvinyl esters, polyethylene, polypropylene, poly(vinyl acetate), poly vinyl chloride, polystyrene, polyvinyl halides, polyvinylpyrrolidone, polymers of acrylic and methacrylic esters, polysiloxanes, polyurethanes and copolymers thereof, modified celluloses, alkyl cellulose, hydroxyalkyl celluloses, cellulose ethers, cellulose esters, nitro celluloses, cellulose acetate, cellulose propionate, cellulose acetate butyrate, cellulose acetate phthalate, carboxyethyl cellulose, cellulose triacetate, cellulose sulfate sodium salt, and polyacrylates such as poly(methyl methacrylate), poly (ethylmethacrylate), poly(butylmethacrylate), poly(isobutylmethacrylate), poly(hexylmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate).

The foregoing materials may be used alone, as physical mixtures (blends), or as co-polymers. In a preferred embodiment, the nanoparticle is formed of polymers fabricated from polylactides (PLA) and copolymers of lactide and glycolide (PLGA). These have established commercial use in humans and have a long safety record (Jiang, et al., *Adv. Drug Deliv. Rev.*, 57(3):391-410); Aguado and Lambert, *Immunobiology*, 184(2-3):113-25 (1992); Bramwell, et al., *Adv. Drug Deliv. Rev.*, 57(9):1247-65 (2005)).

The polymer may be a bioadhesive polymer that is hydrophilic or hydrophobic. Hydrophilic polymers include CARBOPOL™ (a high molecular weight, crosslinked, acrylic acid-based polymers manufactured by NOVEON™), polycarbophil, cellulose esters, and dextran.

Rate controlling polymers may be included in the polymer matrix or in the coating on the formulation. Examples of rate controlling polymers that may be used are hydroxypropylmethylcellulose (HPMC) with viscosities of either 5, 50, 100 or 4000 cps or blends of the different viscosities, ethylcellulose, methylmethacrylates, such as EUDRAGIT® RS100, EUDRAGIT® RL100, EUDRAGIT® NE 30D (supplied by Rohm America). Gastrosoluble polymers, such as EUDRAGIT® E100 or enteric polymers such as EUDRAGIT® L100-55D, L100 and S100 may be blended with rate controlling polymers to achieve pH dependent release kinetics. Other hydrophilic polymers such as alginate, polyethylene oxide, carboxymethylcellulose, and hydroxyethylcellulose may be used as rate controlling polymers.

These polymers can be obtained from sources such as Sigma Chemical Co., St. Louis, Mo.; Polysciences, Warrenton, Pa.; Aldrich, Milwaukee, Wis.; Fluka, Ronkonkoma, N.Y.; and BioRad, Richmond, Calif., or can be synthesized from monomers obtained from these or other suppliers using standard techniques.

B. Antigens

Antigens can be peptides, proteins, polysaccharides, saccharides, lipids, glycolipids, nucleic acids, or combinations thereof. The antigen can be derived from ant source, including, but not limited to, a virus, bacterium, parasite, plant, protozoan, fungus, tissue or transformed cell such as a cancer or leukemic cell and can be a whole cell or immunogenic component thereof, e.g., cell wall components or molecular components thereof.

Suitable antigens are known in the art and are available from commercial government and scientific sources. In one embodiment, the antigens are whole inactivated or attenuated organisms. These organisms may be infectious organisms, such as viruses, parasites and bacteria. These organisms may also be tumor cells. The antigens may be purified or partially purified polypeptides derived from tumors or viral or bacterial sources. Criteria for identifying and selecting effective antigenic peptides (e.g., minimal peptide sequences capable of eliciting an immune response) can be found in the art. For example, Apostolopoulos, et al. (*Curr. Opin. Mol. Ther.*, 2:29-36 (2000)), discusses the strategy for identifying minimal antigenic peptide sequences based on an understanding of the three-dimensional structure of an antigen-presenting molecule and its interaction with both an antigenic peptide and T-cell receptor. Shastri, (*Curr. Opin. Immunol.*, 8:271-7 (1996)), disclose how to distinguish rare peptides that serve to activate T cells from the thousands peptides normally bound to MHC molecules. The antigens can be recombinant polypeptides produced by expressing DNA encoding the polypeptide antigen in a heterologous expression system. The antigens can be DNA encoding all or part of an antigenic protein. The DNA may be in the form of vector DNA such as plasmid DNA.

Antigens may be provided as single antigens or may be provided in combination. Antigens may also be provided as complex mixtures of polypeptides or nucleic acids.

i. Viral Antigens

A viral antigen can be isolated from any virus including, but not limited to, a virus from any of the following viral families: Arenaviridae, Arterivirus, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain))), Flaviviridae, (e.g., Hepatitis C virus, Dengue virus 1, Dengue virus 2, Dengue virus 3, and Dengue virus 4), Hepadnaviridae, Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenzavirus A and B and C), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxviridae (e.g., vaccinia and smallpox virus), Reoviridae (e.g., rotavirus), Retroviridae (e.g., lentivirus, such as human immunodeficiency virus (HIV) 1 and HIV 2), Rhabdoviridae (for example, rabies virus, measles virus, respiratory syncytial virus, etc.), Togaviridae (for example, rubella virus, dengue virus, etc.), and Totiviridae. Suitable viral antigens also include all or part of Dengue protein M, Dengue protein E, Dengue D1NS1, Dengue D1NS2, and Dengue D1NS3.

Viral antigens may be derived from a particular strain such as a papilloma virus, a herpes virus, i.e. herpes simplex 1 and 2; a hepatitis virus, for example, hepatitis A virus (HAV), hepatitis B virus (HBV), hepatitis C virus (HCV), the delta hepatitis D virus (HDV), hepatitis E virus (HEV) and hepatitis G virus (HGV), the tick-borne encephalitis viruses; parainfluenza, varicella-zoster, cytomeglavirus, Epstein-Barr, rotavirus, rhinovirus, adenovirus, coxsackieviruses, equine encephalitis, Japanese encephalitis, yellow fever, Rift Valley fever, and lymphocytic choriomeningitis.

ii. Bacterial Antigens

Bacterial antigens can originate from any bacteria including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus,* Hemophilus influenza type B (HIB), *Hyphomicrobium, Legionella, Leptspirosis, Listeria, Meningococcus* A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus,* and *Treponema, Vibrio,* and *Yersinia.* iii. Parasite Antigens

Parasite antigens can be obtained from parasites such as, but not limited to, an antigen derived from *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis* and *Schistosoma mansoni.* These include Sporozoan antigens, Plasmodian antigens, such as all or part of a Circumsporozoite protein, a Sporozoite surface protein, a liver stage antigen, an apical membrane associated protein, or a Merozoite surface protein.

iv. Allergens and Environmental Antigens

The antigen can be an allergen or environmental antigen, such as, but not limited to, an antigen derived from naturally occurring allergens such as pollen allergens (tree-, herb, weed-, and grass pollen allergens), insect allergens (inhalant, saliva and venom allergens), animal hair and dandruff allergens, and food allergens. Important pollen allergens from trees, grasses and herbs originate from the taxonomic orders of Fagales, Oleales, Pinales and platanaceae including i.a. birch (*Betula*), alder (*Alnus*), hazel (*Corylus*), hornbeam (*Carpinus*) and olive (*Olea*), cedar (*Cryptomeria* and *Juniperus*), Plane tree (*Platanus*), the order of Poales including i.e. grasses of the genera *Lolium, Phleum, Poa, Cynodon, Dactylis, Holcus, Phalaris, Secale,* and *Sorghum,* the orders of Asterales and Urticales including i.a. herbs of the genera *Ambrosia, Artemisia,* and *Parietaria*. Other allergen antigens that may be used include allergens from house dust mites of the genus *Dermatophagoides* and *Euroglyphus*, storage mite e.g *Lepidoglyphys, Glycyphagus* and *Tyrophagus*, those from cockroaches, midges and fleas e.g. *Blatella, Periplaneta, Chironomus* and *Ctenocepphalides*, those from mammals such as cat, dog and horse, birds, venom allergens including such originating from stinging or biting insects such as those from the taxonomic order of *Hymenoptera* including bees (superfamily Apidae), wasps (superfamily Vespidea), and ants (superfamily Formicoidae). Still other allergen antigens that may be used include inhalation allergens from fungi such as from the genera *Alternaria* and *Cladosporium*.

v. Tumor Antigens

The antigen can be a tumor antigen, including a tumor-associated or tumor-specific antigen, such as, but not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, Triosephosphate isomeras, Bage-1, Gage 3,4,5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15 (58), CEA, RAGE, NY-ESO (LAGS), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (Ep-CAM), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, and TPS.

C. Adaptor Elements

Adaptor elements associate with the nanoparticle and provide substrates that facilitate the modular assembly and disassembly of functional elements to the nanoparticle. Adaptor elements may associate with nanoparticles through a variety of interactions including, but not limited to, hydrophobic interactions, electrostatic interactions and covalent coupling.

In a preferred embodiment, the adaptor elements associate with the polymeric nanoparticles noncovalently through hydrophobic interactions. Examples of adaptor elements which may associate with nanoparticles via hydrophobic interactions include, but are not limited to, fatty acids, hydrophobic or amphipathic peptides or proteins, and polymers. These classes of adaptor elements may also be used in any combination or ratio. In a preferred embodiment, the association of adaptor elements with nanoparticles facilitates a prolonged presentation of functional elements which can last for several weeks.

Adaptor elements can also be attached to polymeric nanoparticles through covalent interactions through various functional groups. Functionality refers to conjugation of a molecule to the surface of the particle via a functional chemical group (carboxylic acids, aldehydes, amines, sulfhydryls and hydroxyls) present on the surface of the particle and present on the molecule to be attached.

Functionality may be introduced into the particles in two ways. The first is during the preparation of the nanoparticles, for example during the emulsion preparation of nanoparticles by incorporation of stabilizers with functional chemical groups. Suitable stabilizers include hydrophobic or amphipathic molecules that associate with the outer surface of the nanoparticles.

A second is post-particle preparation, by direct crosslinking particles and ligands with homo- or heterobifunctional crosslinkers. This second procedure may use a suitable chemistry and a class of crosslinkers (CDI, EDAC, glutaraldehydes, etc. as discussed in more detail below) or any other crosslinker that couples ligands to the particle surface via chemical modification of the particle surface after preparation. This second class also includes a process whereby amphiphilic molecules such as fatty acids, lipids or functional stabilizers may be passively adsorbed and adhered to the particle surface, thereby introducing functional end groups for tethering to ligands.

One useful protocol involves the "activation" of hydroxyl groups on polymer chains with the agent, carbonyldiimidazole (CDI) in aprotic solvents such as DMSO, acetone, or THF. CDI forms an imidazolyl carbamate complex with the hydroxyl group which may be displaced by binding the free amino group of a molecule such as a protein. The reaction is an N-nucleophilic substitution and results in a stable N-alkylcarbamate linkage of the molecule to the polymer. The "coupling" of the molecule to the "activated" polymer matrix is maximal in the pH range of 9-10 and normally requires at least 24 hrs. The resulting molecule-polymer complex is stable and resists hydrolysis for extended periods of time.

Another coupling method involves the use of 1-ethyl-3-(3-dimethylaminopropyl)carbodiimide (EDAC) or "water-soluble CDI" in conjunction with N-hydroxylsulfosuccinimide (sulfo NHS) to couple the exposed carboxylic groups of polymers to the free amino groups of molecules in a totally aqueous environment at the physiological pH of 7.0. Briefly, EDAC and sulfo-NHS form an activated ester with the carboxylic acid groups of the polymer which react with the amine end of a molecule to form a peptide bond. The resulting peptide bond is resistant to hydrolysis. The use of sulfo-NHS in the reaction increases the efficiency of the EDAC coupling by a factor of ten-fold and provides for exceptionally gentle conditions that ensure the viability of the molecule-polymer complex.

By using either of these protocols it is possible to "activate" almost all polymers containing either hydroxyl or carboxyl groups in a suitable solvent system that will not dissolve the polymer matrix.

A useful coupling procedure for attaching molecules with free hydroxyl and carboxyl groups to polymers involves the use of the cross-linking agent, divinylsulfone. This method would be useful for attaching sugars or other hydroxylic compounds with bioadhesive properties to hydroxylic matrices. Briefly, the activation involves the reaction of divinylsulfone to the hydroxyl groups of the polymer, forming the vinylsulfonyl ethyl ether of the polymer. The vinyl groups will couple to alcohols, phenols and even amines. Activation and coupling take place at pH 11. The linkage is stable in the pH range from 1-8 and is suitable for transit through the intestine.

Any suitable coupling method known to those skilled in the art for the coupling of molecules and polymers with double bonds, including the use of UV crosslinking, may be used for attachment of molecules to the polymer.

In one embodiment adaptor elements can be conjugated to affinity tags. Affinity tags are any molecular species which form highly specific, noncovalent, physiochemical interactions with defined binding partners. Affinity tags which form highly specific, noncovalent, physiochemical interactions with one another are defined herein as "complementary". Suitable affinity tag pairs are well known in the art and include epitope/antibody, biotin/avidin, biotin/streptavidin, biotin/neutravidin, glutathione-S-transferase/glutathione, maltose binding protein/amylase and maltose binding protein/maltose. Examples of suitable epitopes which may be used for epitope/antibody binding pairs include, but are not limited to, HA, FLAG, c-Myc, glutatione-S-transferase, $His_6$, GFP, DIG, biotin and avidin. Antibodies (both monoclonal and polyclonal and antigen-binding fragments thereof) which bind to these epitopes are well known in the art.

Affinity tags that are conjugated to adaptor elements allow for highly flexible, modular assembly and disassembly of functional elements which are conjugated to affinity tags which form highly specific, noncovalent, physiochemical interactions with complementary affinity tags which are conjugated to adaptor elements. Adaptor elements may be conjugated with a single species of affinity tag or with any combination of affinity tag species in any ratio. The ability to vary the number of species of affinity tags and their ratios conjugated to adaptor elements allows for exquisite control over the number of functional elements which may be attached to the nanoparticles and their ratios.

In another embodiment adaptor elements are coupled directly to functional elements in the absence of affinity tags, such as through direct covalent interactions. Adaptor elements can be covalently coupled to at least one species of functional element. Adaptor elements can be covalently coupled to a single species of functional element or with any combination of species of functional elements in any ratio.

In a preferred embodiment adaptor elements are conjugated to at least one affinity tag that provides for assembly and disassembly of modular functional elements which are conjugated to complementary affinity tags. In a more preferred embodiment, adaptor elements are fatty acids that are conjugated with at least one affinity tag. In a particularly preferred embodiment, the adaptor elements are fatty acids conjugated with avidin or streptavidin. Such avidin/streptavidin-conjugated fatty acids allow for the attachment of a wide variety of biotin-conjugated functional elements.

The adaptor elements are provided on, or in the surface of, nanoparticles at a high density. This high density of adaptor elements allows for coupling of the nanoparticle to a variety of species of functional elements while still allowing for the functional elements to be present in high enough numbers to be efficacious.

i. Fatty Acids

The adaptor elements may include fatty acids. Fatty acids may be of any acyl chain length and may be saturated or unsaturated. In a particularly preferred embodiment the fatty acid is palmitic acid. Other suitable fatty acids include, but are not limited to, saturated fatty acids such as butyric, caproic, caprylic, capric, lauric, myristic, stearic, arachidic and behenic acid. Still other suitable fatty acids include, but are not limited to, unsaturated fatty acids such as oleic, linoleic, alpha-linolenic, arachidonic, eicosapentaenoic, docosahexaenoic and erucic acid.

ii. Hydrophobic or Amphipathic Peptides

The adaptor elements may include hydrophobic or amphipathic peptides. Preferred peptides should be sufficiently hydrophobic to preferentially associate with the polymeric nanoparticle over the aqueous environment. Amphipathic polypeptides useful as adaptor elements may be mostly hydrophobic on one end and mostly hydrophilic on the other end. Such amphipathic peptides may associate with polymeric nanoparticles through the hydrophobic end of the peptide and be conjugated on the hydrophilic end to a functional group.

iii. Hydrophobic Polymers

Adaptor elements may include hydrophobic polymers. Examples of hydrophobic polymers include, but are not limited to, polyanhydrides, poly(ortho)esters, and polyesters such as polycaprolactone.

D. Functional Elements

Functional elements which associate with the nanoparticles provide a number of different functions to the composition. These functions include protection of the nanoparticle vaccine from hostile environments during transit in the gastrointestinal tract, transport through epithelial barriers, targeting antigen presenting cells with high avidity, and transport of mediators that facilitate uptake and presentation of antigen by antigen-presenting cells through disruption of intracellular antigen-sequestering compartments. Functional elements may include dendritic cell recognition elements, epithelial cell recognition elements, pH-sensitive molecules which protect the composition from hydrolysis and degradation in low-pH environments, non-pH-sensitive molecules which protect the composition from hydrolysis and degradation in low-pH environments, and/or endosome-disrupting agents.

Nanoparticles may be associated with a single species of functional element or may be associated with any combination of disclosed functional elements in any ratio. In one embodiment, functional elements are directly associated with nanoparticles in the absence of adaptor elements. Functional elements may be directly associated with nanoparticles through covalent or noncovalent interactions, including, but not limited to, hydrophobic interactions and electrostatic interactions. Covalent attachment of functional elements can be achieved by introducing functionality to the polymeric nanoparticles using methods described above with respect to adaptor elements.

In another embodiment, functional elements are associated with nanoparticles through adaptor elements which directly associate with the nanoparticles. Functional elements may be directly, covalently coupled to adaptor elements or may couple to adaptor elements through complementary affinity tags conjugated to the adaptor and functional elements. Multiple different species of functional elements may be associated with nanoparticles in any desired ratio, for instance, by conjugating each species of functional element to a separate species of affinity tag. These functional elements may then associate with nanoparticles coated with adaptor elements conjugated to an appropriate ratio of complementary affinity tags. Multiple species of functional elements may also be associated with nanoparticles by covalently coupling each species of functional element at a desired ratio to adaptor elements.

In a preferred embodiment, functional elements are conjugated to biotin. Biotin conjugation allows the functional elements to interact with adaptor elements conjugated with avidin, neutravidin or streptavidin.

i. Targeting Molecules for Professional Antigen Presenting Cells

Of the main types of antigen-presenting cells (B cell, macrophages and DCs), the DC is the most potent and is responsible for initiating all antigen-specific immune responses. One biological feature of DCs is their ability to sense conditions under which antigen is encountered, initiating a process of "DC maturation". Using receptors for various microbial and inflammatory products, DCs respond to antigen exposure in different ways depending on the nature of the pathogen (virus, bacteria, protozoan) encountered. This information is transmitted to T cells by altered patterns of cytokine release at the time of antigen presentation in lymph nodes, altering the type of T cell response elicited. Thus, targeting DCs provides the opportunity not only to quantitatively enhance the delivery of antigen and antigen responses in general, but to qualitatively control the nature of the immune response depending on the desired vaccination outcome.

Dendritic cells express a number of cell surface receptors that can mediate the endocytosis of bound antigen. Targeting exogenous antigens to internalizing surface molecules on systemically-distributed antigen presenting cells facilitates uptake of antigens and thus overcomes a major rate-limiting step in immunization and thus in vaccination.

Dendritic cell targeting molecules include monoclonal or polyclonal antibodies or fragments thereof that recognize and bind to epitopes displayed on the surface of dendritic cells. Dendritic cell targeting molecules also include ligands which bind to a cell surface receptor on dendritic cells. One such receptor, the lectin DEC-205, has been used in vitro and in mice to boost both humoral (antibody-based) and cellular (CD8 T cell) responses by 2-4 orders of magnitude (Hawiger, et al., J. Exp. Med., 194(6):769-79 (2001); Bonifaz, et al., J. Exp. Med., 196(12):1627-38 (2002); Bonifaz, et al., J. Exp. Med., 199(6):815-24 (2004)). In these experiments, antigens were fused to an anti-DEC205 heavy chain and a recombinant antibody molecule was used for immunization.

A variety of other endocytic receptors, including a mannose-specific lectin (mannose receptor) and IgG Fc receptors, have also been targeted in this way with similar enhancement of antigen presentation efficiency. Other suitable receptors which may be targeted include, but are not limited to, DC-SIGN, 33D1, SIGLEC-H, DCIR, CD11c, heat shock protein receptors and scavenger receptors.

Other receptors which may be targeted include the toll-like receptors (TLRs). TLRs recognize and bind to pathogen-associated molecular patterns (PAMPs). PAMPs target the TLR on the surface of the dendritic cell and signals internally, thereby potentially increasing DC antigen uptake, maturation and T-cell stimulatory capacity. PAMPs conjugated to the particle surface or co-encapsulated include unmethylated CpG DNA (bacterial), double-stranded RNA (viral), lipopolysacharride (bacterial), peptidoglycan (bacterial), lipoarabinomannin (bacterial), zymosan (yeast), mycoplasmal lipoproteins such as MALP-2 (bacterial), flagellin (bacterial) poly(inosinic-cytidylic) acid (bacterial), lipoteichoic acid (bacterial) or imidazoquinolines (synthetic).

ii. Targeting Molecules for Epithelial Cells

The potential efficacy of nanoparticle vaccine systems is determined in part by their route of administration into the body. While injection (intradermal, intramuscular, intravenous) is an acceptable solution in many cases, having a vaccine product that is orally available will greatly extend its ease of use and applicability on a global scale. For orally administered vaccines, epithelial cells constitute the principal barrier that separates an organism's interior from the outside world. Epithelial cells such as those that line the gastrointestinal tract form continuous monolayers that simultaneously confront the extracellular fluid compartment and the extracorporeal space. Uptake by these gut epithelial cells can be enhanced, and the nanoparticles carried by "transcytosis" to the lymphatics where they have access to dendritic cells.

Through the process of "antigen sampling", underlying mucosal-associated lymphoid tissue sample the environment for the presence of pathogens. This sampling is carried out by an apical to basolateral transcytotic event and is mediated by M cells located in lymphoid follicle-associated epithelium (FAE) throughout the GI tract. In addition, absorptive enterocytes may transport microorganisms or other nanoparticulates to intraepithelial lymphocytes. DCs may perform this function directly, with a population of DCs being intercalated between epithelial cells and extending processes into the gut lumen to sample the microorganisms present.

Adherence to cells is an essential first step in crossing the epithelial barrier by any of these mechanisms. Therefore, in one embodiment, modular nanoparticle vaccines further include epithelial cell recognition elements. Epithelial cell targeting molecules include monoclonal or polyclonal antibodies or bioactive fragments thereof that recognize and bind to epitopes displayed on the surface of epithelial cells. Epithelial cell targeting molecules also include ligands which bind to a cell surface receptor on epithelial cells. Ligands include, but are not limited to, molecules such as polypeptides, nucleotides and polysaccharides.

A variety of receptors on epithelial cells may be targeted by epithelial cell targeting molecules. Examples of suitable receptors to be targeted include, but are not limited to, IgE Fc receptors, EpCAM, selected carbohydrate specificites, dipeptidyl peptidase, and E-cadherin.

iii. Coatings to Inhibit Degradation of Nanoparticle Vaccine Compositions in Extreme pH Environments Vaccine particles administered orally will encounter a corrosive environment in the gastrointestinal (GI) tract with areas of low and high pH, as well as resident degradative enzymes and solubilizing agents. Biodegradable particulates have gained attention as oral vaccines because of their ability to protect antigens on route to immune sites across the intestinal epithelium (O'Hagan and Valiante, *Nat. Rev. Drug Discov.,* 2(9):727-35 (2003); van der Lubben, et al., *Adv. Drug Deliv. Rev.,* 52(2):139-44 (2001); Wikingsson and Sjoholm, *Vaccine,* 20(27-28):3355-63 (2002); Moser, et al., *Expert Rev. Vaccines,* 2(2):189-96 (2003)). However, while the antigen is protected from environmental elements in transit, little protection is offered to elements coupled to the surface of the particle during the transit to immune effector sites. This protection may be necessary to insure proper particle function and targeting.

For this reason, 'shielding' is a desired feature to protect the nanoparticulate and its immune recognition elements in transit to the GI epithelium. This shielding may be environmentally-sensitive, i.e. pH responsive, or simply a protective layer. In a preferred embodiment, modular nanoparticle vaccines further include pH-sensitive molecules which protect the composition from hydrolysis and degradation in low pH environments. Such pH-sensitive protecting molecules are preferred because subsequent to the particles transit through a low pH environment, upon reaching its destination in the higher pH intestinal site, particles should expose epithelial targeting molecules to allow for specific interactions with target epithelial cells, followed by transcytosis through the epithelium and subsequent interactions with subepithelial dendritic cells.

Preferred non-pH-sensitive molecules which protect the composition from hydrolysis and degradation in low pH environments are poly(ethylene) glycol, gelatin and albumins.

Preferred pH-sensitive molecules which protect the composition from hydrolysis and degradation in low pH environments are elastin and poly(methacrylic) acid (PMAA). Both of these molecules are in extended conformations at pH 7.4 and shrink rapidly (within seconds) upon exposure to lower pH environments (below pH 5 for elastin and below pH 5-6 for poly(methacylic) acid). Other pH-sensitive molecules which may be used include poly(acrylic acid), poly(methyl methacrylic acid) and poly(N-alkyl acrylamides), or other enteric coatings discussed above.

pH-sensitive or pH-insensitive protective molecules may be directly coupled to nanoparticles, or may be coupled to nanoparticles through adaptor elements, such as those described above. In a preferred embodiment the epithelial cell targeting molecules are functionally coupled to adaptor elements.

E. Disruptors of Endosomal Compartments

Many receptors which may be used for targeting modular nanoparticle vaccines to dendritic cells, such as DEC-205, have the property of delivering antigens to late endosomal elements that serve as efficient sites for the formation of immunogenic peptides and their loading onto MHC class II molecules (which are needed for CD4 T cell and antibody responses) (Mellman, *Adv. Exp. Med. Biol.,* 560:63-7; Mellman and Steinman, *Cell,* 106(3):255-8 (2001)). Effective vaccination, however, often requires the production of CD8 cytotoxic T cell responses which occurs only when antigen is present in the cytoplasm. DCs are adept at this function by the process of "cross-presentation", whereby exogenous antigens escape endocytic vesicles and enter the cytoplasm where they are cleaved into peptides by the proteosome, imported into the endoplasmic reticulum, and loaded onto newly synthesized MHC class I molecules (which are required for stimulation of CD8 T cells).

It is possible to greatly enhance the efficiency of cross presentation by artificially causing the limited disruption of endosome-lysosome membranes during antigen uptake. In one embodiment, the modular nanoparticulate vaccine compositions include an agent which causes the disruption of endosomal membranes. Endosomal membrane disrupting agents include, but are not limited to, small molecule drugs, peptides, polypeptides, including elastin, and synthetic agents that disrupt intracellular pH or vesicular membranes.

In a preferred embodiment, the endosome-disrupting agent is a low pH-activated, amphipathic, pore-forming peptide. In a particularly preferred embodiment, the low pH-activated, amphipathic, pore-forming peptide is the commercially-available Endoporter (Endoporter; GeneTools, Philomath, Oreg.) (Summerton, *Ann. N.Y. Acad. Sci.,* 1058:1-14 (2005)).

The endosome-disrupting agent may be encapsulated into the polymeric core of the nanoparticle. Additionally, or alternatively, the endosome-disrupting agent may be attached to the surface of the nanoparticle by association with attached adaptor elements.

G. Adjuvants

The modular nanoparticulate vaccines can include adjuvants. These can be incorporated into, administered with, or administered separately from, the vaccine nanoparticles. Adjuvants may be provided encapsulated or otherwise entrapped in the polymeric core of the nanoparticle vaccine, or may be associated with the surface of the nanoparticle either through direct association with the polymeric core, or through association with adaptor elements. Adjuvant may be in the form of separate nanoparticles or in a suspension or solution administered with the vaccine nanoparticles.

In one embodiment the adjuvant is the synthetic glycolipid alpha-galactosylceramide (αGalCer). Dendritic cells presenting antigens in the context of CD1d can lead to rapid innate and prolonged production of cytokines such as interferon and IL-4 by natural killer T cells (NKT cells). CD1d is a major histocompatibility complex class I-like molecule that presents glycolipid antigens to a subset of NKT cells. Advantageously, αGalCer is not toxic to humans and has been shown to act as an adjuvant, priming both antigen-specific CD4+ and CD8+ T cell responses. For example, it has been shown that αGalCer in conjunction with a malaria vaccine can lead to cytotoxic responses against infected cells, which is an ideal scenario for vaccines against infectious diseases. In addition to αGalCer, other glycolipids that function as adjuvants to activate NKT cell-mediated immune responses can be used.

In another embodiment the adjuvant can be, but is not limited to, one or more of the following: oil emulsions (e.g., Freund's adjuvant); saponin formulations; virosomes and viral-like particles; bacterial and microbial derivatives including, but not limited to carbohydrates such as lipopolysachharide (LPS); immunostimulatory oligonucleotides; ADP-ribosylating toxins and detoxified derivatives; alum; BCG; mineral-containing compositions (e.g., mineral salts, such as aluminium salts and calcium salts, hydroxides, phosphates, sulfates, etc.); bioadhesives and/or mucoadhesives; microparticles; liposomes; polyoxyethylene ether and polyoxyethylene ester formulations; polyphosphazene; muramyl peptides; imidazoquinolone compounds; and surface active substances (e.g. lysolecithin, pluronic polyols, polyanions, peptides, oil emulsions, keyhole limpet hemocyanin, and dinitrophenol).

Adjuvants may also include immunomodulators such as cytokines, interleukins (e.g., IL-1, IL-2, IL-4, IL-5, IL-6, IL-7, IL-12, etc.), interferons (e.g., interferon-.gamma.), macrophage colony stimulating factor, and tumor necrosis factor; and co-stimulatory molecules, such as those of the B7 family. Such proteinaceous adjuvants may be provided as the full-length polypeptide or an active fragment thereof, or in the form of DNA, such as plasmid DNA.

H. Contrast Agents and Other Markers

Optionally, modular nanoparticulate vaccine may further include agents useful for determining the location of administered particles. Agents useful for this purpose include fluorescent tags, radionuclides and contrast agents.

Suitable imaging agents include, but are not limited to, fluorescent molecules such as those described by Molecular Probes (Handbook of fluorescent probes and research products), such as Rhodamine, fluorescein, Texas red, Acridine Orange, Alexa Fluor (various), Allophycocyanin, 7-aminoactinomycin D, BOBO-1, BODIPY (various), Calcien, Calcium Crimson, Calcium green, Calcium Orange, 6-carboxyrhodamine 6G, Cascade blue, Cascade yellow, DAPI, DiA, DID, Di1, DiO, DiR, ELF 97, Eosin, ER Tracker Blue-White, EthD-1, Ethidium bromide, Fluo-3, Fluo4, FM1-43, FM4-64, Fura-2, Fura Red, Hoechst 33258, Hoechst 33342, 7-hydroxy-4-methylcoumarin, Indo-1, JC-1, JC-9, JOE dye, Lissamine rhodamine B, Lucifer Yellow CH, LysoSensor Blue DND-167, LysoSensor Green, LysoSensor Yellow/Blu, Lysotracker Green FM, Magnesium Green, Marina Blue, Mitotracker Green FM, Mitotracker Orange CMTMRos, MitoTracker Red CMXRos, Monobromobimane, NBD amines, NeruoTrace 500/525 green, Nile red, Oregon Green, Pacific Blue. POP-1, Propidium iodide, Rhodamine 110, Rhodamine Red, R-Phycoerythrin, Resorfin, RH414, Rhod-2, Rhodamine Green, Rhodamine 123, ROX dye, Sodium Green, SYTO blue (various), SYTO green (Various), SYTO orange (various), SYTOX blue, SYTOX green, SYTOX orange, Tetramethylrhodamine B, TOT-1, TOT-3, X-rhod-1, YOYO-1, YOYO-3.

Additionally radionuclides can be used as imaging agents. Suitable radionuclides include, but are not limited to radioactive species of Fe(III), Fe(II), Cu(II), Mg(II), Ca(II), and Zn(I1) Indium, Gallium and Technetium. Other suitable contrast agents include metal ions generally used for chelation in paramagnetic T1-type MIR contrast agents, and include di- and tri-valent cations such as copper, chromium, iron, gadolinium, manganese, erbium, europium, dysprosium and holmium. Metal ions that can be chelated and used for radionuclide imaging, include, but are not limited to metals such as gallium, germanium, cobalt, calcium, indium, iridium, rubidium, yttrium, ruthenium, yttrium, technetium, rhenium, platinum, thallium and samarium. Additionally metal ions known to be useful in neutron-capture radiation therapy include boron and other metals with large nuclear cross-sections. Also suitable are metal ions useful in ultrasound contrast, and X-ray contrast compositions.

Examples of other suitable contrast agents include gases or gas emitting compounds, which are radioopaque.

I. Pharmaceutically Acceptable Excipients

The compositions may be administered in combination with a physiologically or pharmaceutically acceptable carrier, excipient, or stabilizer. The term "pharmaceutically acceptable" means a non-toxic material that does not interfere with the effectiveness of the biological activity of the active ingredients. The term "pharmaceutically-acceptable carrier" means one or more compatible solid or liquid fillers, dilutants or encapsulating substances which are suitable for administration to a human or other vertebrate animal. The term "carrier" refers to an organic or inorganic ingredient, natural or synthetic, with which the active ingredient is combined to facilitate the application.

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen.

Optional pharmaceutically acceptable excipients include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as crosslinked PVP (POLYPLASDONE® XL from GAF Chemical Corp).

Stabilizers are used to inhibit or retard decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-b-alanine, sodium N-lauryl-b-iminodipropionate, myristoamphoacetate, lauryl betaine and lauryl sulfobetaine.

If desired, the particles may also contain minor amount of nontoxic auxiliary substances such as wetting or emulsifying agents, dyes, pH buffering agents, or preservatives.

The particles may be complexed with other agents. The pharmaceutical compositions may take the form of, for example, tablets or capsules prepared by conventional means with pharmaceutically acceptable excipients such as binding agents (e.g., acacia, methylcellulose, sodium carboxymethylcellulose, polyvinylpyrrolidone (Povidone), hydroxypropyl methylcellulose, sucrose, starch, and ethylcellulose); fillers (e.g., corn starch, gelatin, lactose, acacia, sucrose, microcrystalline cellulose, kaolin, mannitol, dicalcium phosphate, calcium carbonate, sodium chloride, or alginic acid); lubricants (e.g. magnesium stearates, stearic acid, silicone fluid, talc, waxes, oils, and colloidal silica); and disintegrators (e.g. micro-crystalline cellulose, corn starch, sodium starch glycolate and alginic acid. If water-soluble, such formulated complex then may be formulated in an appropriate buffer, for example, phosphate buffered saline or other physiologically compatible solutions. Alternatively, if the resulting complex has poor solubility in aqueous solvents, then it may be formulated with a non-ionic surfactant such as TWEEN™, or polyethylene glycol. Thus, the compounds and their physiologically acceptable solvates may be formulated for administration.

Liquid formulations for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation by the patient.

The particles may be further coated. Suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Rohm Pharma, Darmstadt, Germany), zein, shellac, and polysaccharides. Additionally, the coating material may contain conventional carriers such as plasticizers, pigments, colorants, glidants, stabilization agents, pore formers and surfactants.

III. Methods and Materials for Manufacture and Formulation of Nanoparticulate Vaccine Compositions A. Methods of Making Antigen-Encapsulated Nanoparticles Many different processes can be used to form the nanoparticles. If the process does not produce particles having a homogenous size range, then the particles can be separated using standard techniques such as sieving to produce a population of particles having the desired size range.

i. Solvent Evaporation

Methods for forming nanoparticles using solvent evaporation techniques are described in E. Mathiowitz, et al., *J. Scanning Microscopy*, 4:329 (1990); Beck, et al., *Fertil. Steril.*, 31:545 (1979); Beck, et al., *Am. J. Obstet. Gynecol.*, 135(3) (1979); Benita, et al., *J. Pharm. Sci.*, 73:1721 (1984); and U.S. Pat. No. 3,960,757 to Morishita, et al. The polymer is dissolved in a volatile organic solvent, such as methylene chloride. A substance to be incorporated optionally is added to the solution, and the mixture is suspended in an aqueous solution that contains a surface active agent such as poly (vinyl alcohol). Substances which can be incorporated in the nanoparticles include, but are not limited to, antigens, adjuvants, imaging agents, endosome-disrupting agents and contrast agents. The resulting emulsion is stirred until most of the organic solvent evaporated, leaving solid nano- and microparticles.

In a preferred embodiment, antigen-loaded, spherical PLGA nanoparticles with a mean diameter of 100-200 nm and protein loadings of up to 40% are produced by a modified version of this technique. In this method, 100 mg of PLGA is dissolved in 2 ml of methylene chloride in a short glass test tube (5.8 cm long, diameter 1.2 cm) overnight. To this solution, approximately 100-200 ul of the concentrated antigen solution is added and vortexed rapidly. This solution is added drop wise to 4 ml of an aqueous solution of 5% poly (vinyl alcohol) while vortexing. The emulsion formed is further sonicated three times for intervals of 10 seconds each at 38% amplitude (Tekmar Soni Disrupter model TM300, 40% duty cycle, microtip #4) to yield a homogeneous milky mixture. The single emulsion is poured into 100 ml of PVA 0.3%. The polymer/PVA dispersion is stirred on a magnetic stir plate for 3 hours at room temperature to allow for adequate solvent evaporation. Once solidified, the nanospheres are isolated by centrifugation (12000 rpm, 4° C., 10 minutes). The supernatant is discarded. Nanospheres are washed three times with deionized water (10 ml) to remove excess of PVA before they are frozen at −80° C. and then lyophilized for 48 hours. All parameters of this method are easily scaled to produce different batch sizes of nanoparticles.

This method is useful for relatively stable polymers like polyesters and polystyrene. However, labile polymers, such as polyanhydrides, may degrade during the fabrication process due to the presence of water. For these polymers, some of the following methods performed in completely anhydrous organic solvents are more useful.

ii. Hot Melt Microencapsulation

Microspheres can be formed from polymers such as polyesters and polyanhydrides using hot melt microencapsulation methods as described in Mathiowitz, et al., *Reactive Polymers*, 6:275 (1987). In this method, the use of polymers with molecular weights between 3-75,000 daltons is preferred. In this method, the polymer first is melted and then mixed with the solid particles of a substance to be incorporated that have been sieved to less than 50 microns. The mixture is suspended in a non-miscible solvent (like silicon oil), and, with continuous stirring, heated to above the melting point of the polymer, for example, 5° C. Once the emulsion is stabilized, it is cooled until the polymer particles solidify. The resulting micro spheres are washed by decanting with petroleum ether to give a free-flowing powder. Microspheres with sizes between one to 1000 microns are obtained with this method.

iii. Solvent Extraction

This technique is primarily designed for polyanhydrides and is described, for example, in WO 93/21906 to Brown University Research Foundation. In this method, the substance to be incorporated is dispersed or dissolved in a solution of the selected polymer in a volatile organic solvent, such as methylene chloride. This mixture is suspended by stirring in an organic oil, such as silicon oil, to form an emulsion. Microspheres that range between 1-300 microns can be obtained by this procedure.

iv. Spray-Drying

Methods for forming microspheres using spray drying techniques are described in U.S. Pat. No. 6,620,617, to Mathiowitz et al. In this method, the polymer is dissolved in an organic solvent such as methylene chloride or in water. A known amount of an agent to be incorporated is suspended (insoluble agent) or co-dissolved (soluble agent) in the polymer solution. The solution or the dispersion then is spray-dried. Microspheres ranging between 0.1-10 microns are obtained.

v. Phase Inversion

Microspheres can be formed from polymers using a phase inversion method wherein a polymer is dissolved in a "good" solvent, fine particles of a substance to be incorporated, such as a drug, are mixed or dissolved in the polymer solution, and the mixture is poured into a strong non-solvent for the polymer, to spontaneously produce, under favorable conditions, polymeric microspheres, wherein the polymer is either coated with the particles or the particles are dispersed in the polymer. The method can be used to produce microparticles in a wide range of sizes, including, for example, about 100 nanometers to about 10 microns. Exemplary polymers which can be used include polyvinylphenol and polylactic acid. Substances which can be incorporated include, for example, imaging agents such as fluorescent dyes, or biologically active molecules such as proteins or nucleic acids. In the process, the polymer is dissolved in an organic solvent and then contacted with a non-solvent, which causes phase inversion of the dissolved polymer to form small spherical particles, with a narrow size distribution optionally incorporating an antigen or other substance.

B. Methods of Attaching Adaptor Elements to Nanoparticles

Adaptor elements may be conjugated to affinity tags prior to, or after their association with polymeric nanoparticles. In a preferred embodiment, the adaptor elements are fatty acids and the affinity tag is avidin/streptavidin. In a more preferred embodiment, palmitic acid is conjugated to avidin. In one method, avidin is dissolved at a concentration of 5 mg/ml in 37° C. prewarmed 2 ml solution of 2% deoxycholate in 1×PBS. To this solution, a 10 fold molar excess of NHS-Palmitic acid is added and the solution is stirred and sonicated in 37° C. water bath (Branson, 50 kHz freq.). The reaction is maintained at 37° C. for 24 hours after which excess palmitic acid is removed by dialysis against a 0.15% deoxycholate-PBS buffer prewarmed to 37° C. After three buffer changes, the avidin-palmitic acid conjugate is verified by reverse phase HPLC on a Prevail C18 column with a linear methanol gradient in 1×PBS as the mobile phase and UV detection at 280 nm. This method is easily adapted to conjugate avidin to any fatty acid of choice.

Avidin may be coupled to peptides and polymers by similar techniques. The chemistry involved in the coupling reaction will depend on the nature of available functional groups on the fatty acid, peptide or polymer. Methods for conjugating avidin to fatty acids, peptides and polymers are well known in the art. Methods for conjugating other affinity tags such as biotin, epitope tags (HA, FLAG, c-myc) and antibodies to fatty acids, peptides and polymers are well known in the art.

In a preferred embodiment, adaptor elements such as those described above, including fatty acids, hydrophobic or aliphatic peptides, and polymers, are conjugated onto the surface of nanoparticles at the emulsion stage of nanoparticle preparation. In a particularly preferred embodiment, the nanoparticles include PLGA and the adaptor elements include avidin-conjugated palmitic acid. In one method, dissolved PLGA solution is added to a 4 ml solution of 2 parts avidin-palmitic acid, 2 parts 5% PVA. A 50:50 mixture of protein-palmitic acid conjugates and 5% PVA has been found to yield optimal surface coverage of avidin groups on nano-sized particles.

C. Methods of Attaching Functional Elements to Adaptor Elements

Functional elements can routinely be assembled onto adaptor elements incorporated onto the nanoparticle surface by conjugating the functional elements to affinity tags which are complementary to the affinity tags conjugated to the adaptor elements. Especially useful affinity tag pairs for use in coupling adaptor elements to functional elements are biotin-avidin and biotin-streptavidin. Affinity tag-conjugated functional elements are incubated with nanoparticles pre-coated with adaptor elements conjugated to complementary affinity tags under any appropriate buffer, salt and detergent conditions. For example, typical incubations may be performed at 4° C. for 2-4 hours, 37° C. for 20 minutes or room temperature for 1 hour. Incubations may be performed in phosphate buffered saline or other buffer compositions adjusted to a pH between 6.0 and 7.4. Incubation may occur with gentle shaking, rocking or rotation. Nanoparticles may then be washed with excess incubation buffer to remove unbound or non-specifically bound functional elements.

Functional elements may also be conjugated directly to adaptor elements in the absence of affinity tags, either prior to, or after their association with polymeric nanoparticles. Methods for conjugating functional elements such as peptides, polypeptides, polymers and antibodies to adaptor elements such as fatty acids, peptides and polymers are well known in the art. For example, fatty acids such as palmitic acid may be conjugated to the C-terminus of peptides, polypeptides and antibodies using a methodology similar to that described above for conjugation of palmitic acid to avidin.

IV. Methods of Using Nanoparticulate Vaccine Compositions

The nanoparticle vaccine compositions disclosed herein are useful for activating T cells in subjects for prophylactic and therapeutic applications. Activation of T cells by nanoparticle vaccine compositions increases their proliferation, cytokine production, differentiation, effector functions and/or survival. Methods for measuring these are well known to those in the art. The T cells activated by the nanoparticle vaccine compositions can be any cell which express the T cell receptor, including $\alpha/\beta$ and $\gamma/\delta$ T cell receptors. T-cells include all cells which express CD3, including T-cell subsets which also express CD4 and CD8. T-cells include both naive and memory cells and effector cells such as CTL. T-cells also include regulatory cells such as Th1, Tc1, Th2, Tc2, Th3, Treg, and Tr1 cells. T-cells also include NKT-cells and similar unique classes of the T-cell lineage. In preferred embodiments the T cells that are activated are $CD8^+$ T cells. As demonstrated in the examples below, the aAPCs disclosed herein preferentially activate and expand $CD8^+$ T cells when activated ex vivo.

A. Subjects to be Treated

In general, the compositions described herein are useful for treating a subject having or being predisposed to any disease or disorder to which the subject's immune system mounts an immune response. The compositions are useful as prophylactic vaccines, which confer resistance in a subject to subsequent exposure to infectious agents. The compositions are also useful as therapeutic vaccines, which can be used to initiate or enhance a subject's immune response to a pre-existing antigen, such as a tumor antigen in a subject with cancer, or a viral antigen in a subject infected with a virus. The compositions are also useful as desensitizing vaccines, which function to "tolerize" an individual to an environmental antigen, such as an allergen.

The ability to target these compositions to professional antigen-presenting cells such as dendritic cells, and the ability of these compositions to elicit T-cell mediated immune responses by causing cross-presentation of antigens makes these compositions especially useful for eliciting a cell-mediated response to a disease-related antigen in order to attack the disease. Thus, in a preferred embodiment, the type of disease to be treated or prevented is a malignant tumor or a chronic infectious disease caused by a bacterium, virus, protozoan, helminth, or other microbial pathogen that enters intracellularly and is attacked, i.e., by the cytotoxic T lymphocytes.

The desired outcome of a prophylactic, therapeutic or desensitized immune response may vary according to the disease, according to principles well known in the art. For example, an immune response against an infectious agent may completely prevent colonization and replication of an infectious agent, affecting "sterile immunity" and the absence of any disease symptoms. However, a vaccine against infectious agents may be considered effective if it reduces the number, severity or duration of symptoms; if it reduces the number of individuals in a population with symptoms; or reduces the transmission of an infectious agent. Similarly, immune responses against cancer, allergens or infectious agents may completely treat a disease, may alleviate symptoms, or may be one facet in an overall therapeutic intervention against a disease. For example, the stimulation of an immune response against a cancer may be coupled with surgical, chemotherapeutic, radiologic, hormonal and other immunologic approaches in order to affect treatment.

i. Subjects Infected With or Exposed to Infectious Agents

Subjects with or exposed to infectious agents can be treated therapeutically or prophylactically with nanoparticle vaccine compositions disclosed herein. Infectious agents include bacteria, viruses and parasites. In some instances, the subject can be treated prophylactically, such as when there may be a risk of developing disease from an infectious agent. An individual traveling to or living in an area of endemic infectious disease may be considered to be at risk and a candidate for prophylactic vaccination against the particular infectious agent. Preventative treatment can be applied to any number of diseases where there is a known relationship between the particular disease and a particular risk factor, such as geographical location or work environment.

ii. Subjects With or a Risk of Developing Malignant Tumors

In a mature animal, a balance usually is maintained between cell renewal and cell death in most organs and tissues. The various types of mature cells in the body have a given life span; as these cells die, new cells are generated by the proliferation and differentiation of various types of stem cells. Under normal circumstances, the production of new cells is so regulated that the numbers of any particular type of cell remain constant. Occasionally, though, cells arise that are no longer responsive to normal growth-control mechanisms. These cells give rise to clones of cells that can expand to a considerable size, producing a tumor or neoplasm. A tumor that is not capable of indefinite growth and does not invade the healthy surrounding tissue extensively is benign. A tumor that continues to grow and becomes progressively invasive is malignant. The term cancer refers specifically to a malignant tumor. In addition to uncontrolled growth, malignant tumors exhibit metastasis. In this process, small clusters of cancerous cells dislodge from a tumor, invade the blood or lymphatic vessels, and are carried to other tissues, where they continue to proliferate. In this way a primary tumor at one site can give rise to a secondary tumor at another site. The compositions and method described herein may be useful for treating subjects having malignant tumors.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. A melanoma is a type of carcinoma of the skin for which this invention is particularly useful. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The types of cancer that can be treated in with the provided compositions and methods include, but are not limited to, the following: bladder, brain, breast, cervical, colo-rectal, esophageal, kidney, liver, lung, nasopharangeal, pancreatic, prostate, skin, stomach, uterine, and the like. Administration is not limited to the treatment of an existing tumor or infectious disease but can also be used to prevent or lower the risk of developing such diseases in an individual, i.e., for prophylactic use. Potential candidates for prophylactic vaccination include individuals with a high risk of developing cancer, i.e., with a personal or familial history of certain types of cancer.

iii. Subjects Exposed to Allergens

The vaccine compositions may be administered to subjects for the purpose of preventing and/or attenuating allergic reactions, such as allergic reactions which lead to anaphylaxis. Allergic reactions may be characterized by the $T_H2$ responses against an antigen leading to the presence of IgE antibodies. Stimulation of $T_H1$ immune responses and the production of IgG antibodies may alleviate allergic disease. Thus, the disclosed vaccine compositions may lead to the production of antibodies that prevent and/or attenuate allergic reactions in subjects exposed to allergens.

iv. Subjects With Immunosuppressed Conditions

Nanoparticle vaccines disclosed herein can be used for treatment of disease conditions characterized by immunosuppression, including, but not limited to, AIDS or AIDS-related complex, idiopathic immuno suppression, drug induced immunosuppression, other virally or environmentally-induced conditions, and certain congenital immune deficiencies. Nanoparticle vaccine compositions can also be employed to increase immune function that has been impaired by the use of radiotherapy of immunosuppressive drugs (e.g., certain chemotherapeutic agents), and therefore can be particularly useful when used in conjunction with such drugs or radiotherapy.

B. Methods of Administration

In general, methods of administering vaccines are well known in the art. Any acceptable method known to one of ordinary skill in the art may be used to administer a formulation to the subject. The administration may be localized (i.e., to a particular region, physiological system, tissue, organ, or cell type) or systemic. Vaccines can be administered by a number of routes including, but not limited to: oral, inhalation (nasal or pulmonary), intravenous, intraperitoneal, intramuscular, transdermal, subcutaneous, topical, sublingual, or rectal means. Injections can be e.g., intravenous, intradermal, subcutaneous, intramuscular, or intraperitoneal. In some embodiments, the injections can be given at multiple locations.

The nanoparticle vaccines disclosed herein are particularly suitable for enteral administration. The ability to target vaccine compositions to epithelial cells in the digestive tract greatly facilitates the ability of a vaccine to induce mucosal and systemic immunity when administered orally. Molecules, as described above, which protect the vaccine composition and its constituents from hydrolysis and degradation in low pH environments also enhance the efficacy of vaccines administered orally.

Administration of the formulations may be accomplished by any acceptable method which allows an effective amount of the vaccine to reach its target. The particular mode selected will depend upon factors such as the particular formulation, the severity of the state of the subject being treated, and the dosage required to induce an effective immune response. As generally used herein, an "effective amount" is that amount which is able to induce an immune response in the treated subject. The actual effective amounts of vaccine can vary according to the specific antigen or combination thereof being utilized, the particular composition formulated, the mode of administration, and the age, weight, condition of the individual being vaccinated, as well as the route of administration and the disease or disorder.

EXAMPLES

The present invention may be further understood by reference to the following non-limiting examples.

Example 1

Immune Cell-Specific Targeting of Nanoparticles

Materials and Methods:
Cells were adjusted to a concentration of $1\times10^7$ cells/ml in complete media. Plates were coated with various concentrations of anti-CD3ε antibodies according to established protocols. $2\times10^5$ cells were plated per well. Cells were treated with 20 nM complexes either loaded or unloaded with doxorubicin and incubated at 37° C., 5% $CO_2$. On day 3 T cell proliferation was analyzed with a colorimetric assay for quantification of cell proliferation and viability, WST-1®, according to manufacturer's protocol (Roche Diagnostics GmbH, Pennsburg, Germany).

Results:
Using avidin as an adaptor element coupled to fatty acid chains which insert readily into PLGA particles during fabrication, biotinylated antibodies and recombinant proteins that target different immune system cells were attached to the surface of the particles. These surface-modified particles interact specifically with cells and provide effective delivery of anti-proliferative drugs to intracellular compartments. For example, when modified with an antibody that recognizes T cells, Doxorubicin-loaded particles specifically reduced the proliferation of those cells (FIG. 1). Similar results were shown by targeting antigen-presenting cells using nanoparticulates presenting recombinant T cell receptors. These data demonstrate the utility of modular domains for directing nanoparticles to specific subsets of target cells. These data indicate that this approach can be extrapolated to target nanoparticles to other cell types, such as epithelial cells and dendritic cells by incorporating targeting modules onto nanoparticles specific to these cell types.

Example 2

Surface Modification of Nanoparticles with Immune Modulators Increases the Elicited Immune Response Materials and Methods:
Nanoparticles were prepared by a water-oil-water emulsion method using 50:50 Poly(DL-lactide-co-glycolide) from Lactel® with an inherent viscosity of 0.59 dL/g. PLGA was dissolved in methylene chloride. For loaded particles, aqueous solutions of 10 mg chicken egg albumin (ovalbumin, OVA—antigen) was emulsified into the dissolved polymer and sonicated for 30 seconds on ice (Tekmar, Model: TMX400). The resulting water in oil emulsion was subsequently added dropwise into the surfactant (5% Polyvinyl alcohol) (PVA, Sigma-Aldrich®)) and sonicated again for 30 seconds. This was added to a stirring 0.3% PVA solution surfactant solution. After 3 hours particles were centrifuged at 12,000 RPM for 20 minutes and washed with DI water three times, frozen at −80° C., and lyophilized. LPS-coated particles were prepared with 20 mg/ml lipopolysaccharide (Sigma®, from *Escherichia coil*) in the surfactant. Nanoparticles were stored after lyophilization at −20° C. Nanospheres were characterized using scanning electron microscopy. Protein encapsulation was quantified by dissolving the particles in DMSO for 24 hr and performing a BCA Protein Assay (Pierce®).

Results:
Nanoparticulates encapsulating the model antigen, ovalbumin, were surface modified with lipopolysaccharide (LPS) and used to induce immunity in live animals against ovalbumin. LPS is a principal component of the cell wall of gram-negative bacteria and is a ligand for Toll like receptor 4, a major inducer of DC maturation and thus of T cell responsiveness (Reis e Sousa, *Semin. Immunol.*, 16(1):27-34 (2004); Bellou, et al., *Curr. Opin. Allergy Alin. Immunol.*, 3(6):487-94 (2003)). This biological property of LPS was exploited to engineer an immunogenic stimulus onto nanoparticles. LPS consists of a hydrophobic fatty acid chain conjugated to hydrophilic polysaccharide chains (Mayer, *Methods in Microbiology*, 18:157-207 (1985)). LPS is thus a similar composition to protein-fatty acid conjugates and serves as a model for incorporating protein-fatty acid conjugates onto PLGA nanoparticles for engineering high density protein display on the surface.

Figure 2A:
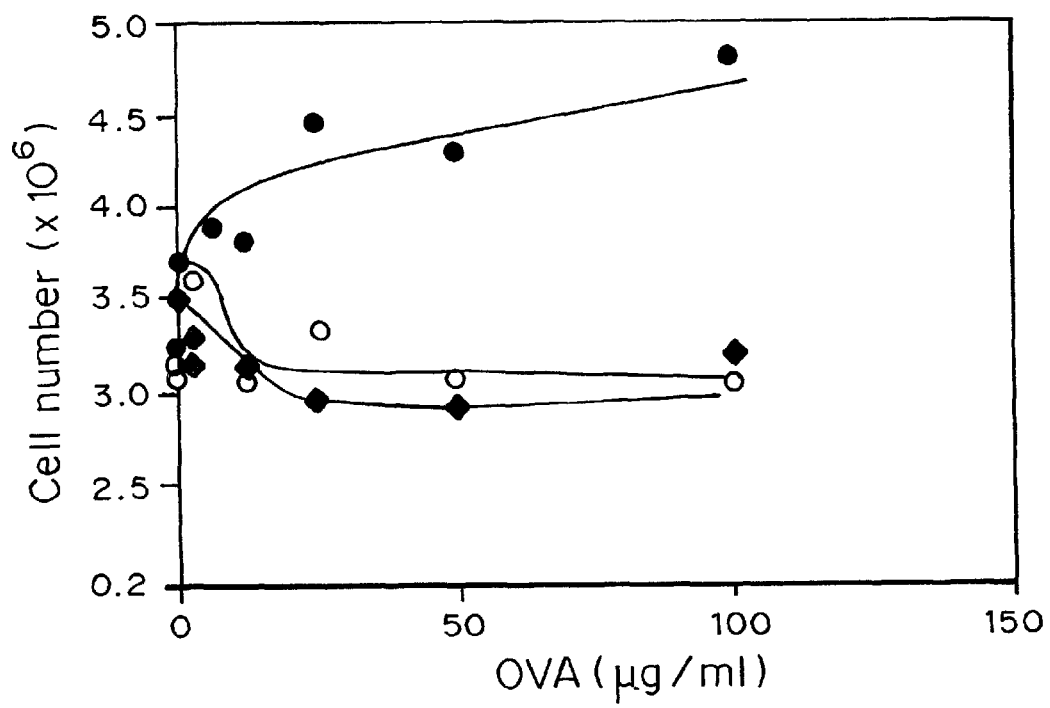
FIG. 2A is a graph showing that spleen cells obtained from mice three days after subcutaneous immunization with ovalbumin-encapsulated, LPS-modified, nanoparticles (-•-) proliferated (number of cells×$10^6$) in response to immobilized ovalbumin, thus demonstrating memory to the antigen. Controls are immobilized antigen (-○-) and blank nanoparticles (-♦-).
Figure 2B:
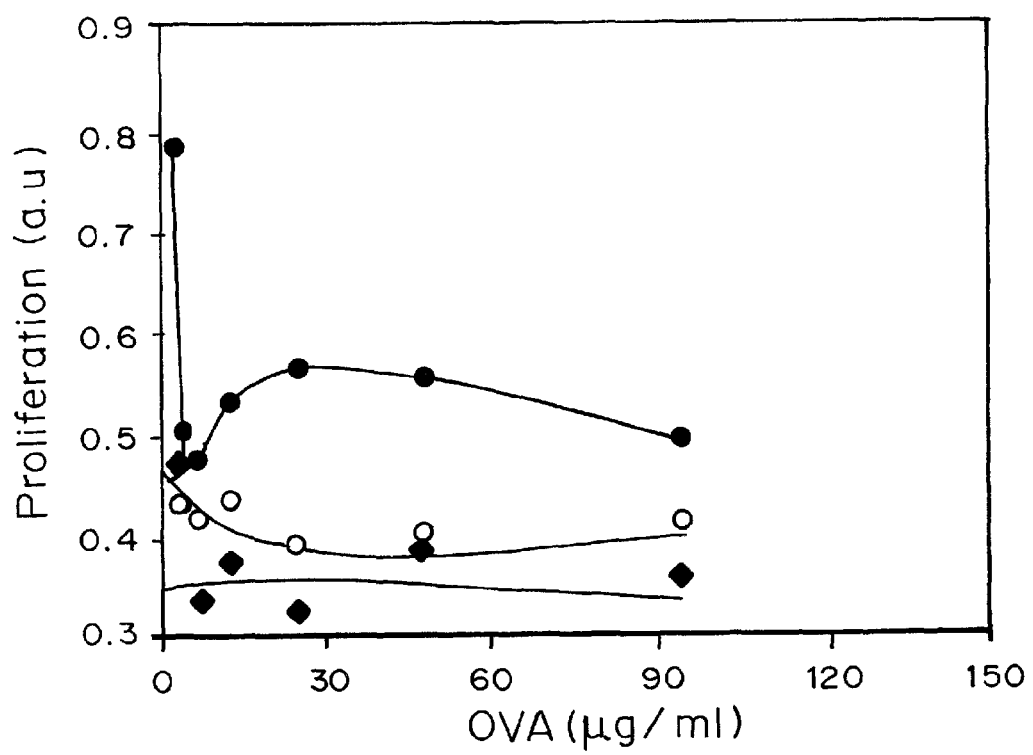
FIG. 2B is a graph showing that spleen cells obtained from mice following oral immunization with ovalbumin-encapsulated, LPS-modified, nanoparticles (-•-) proliferated (absorbance) in response to immobilized ovalbumin, demonstrating the efficacy of the particles in inducing immunity through oral administration. Controls are immobilized (-○-) antigen and blank nanoparticles (-♦-).

Only three days after immunization by subcutaneous injection, spleen cells isolated from injected mice showed a remarkable memory to the injected ovalbumin (FIG. 2A), as evidenced by proliferation of cells to immobilized antigen in a plate. This enhanced response was not observed with mice immunized with particles encapsulating the ovalbumin without LPS or with blank particles. Similar results were observed when animals were fed LPS-modified and unmodified particles (FIG. 2B), demonstrating the efficacy of this approach in inducing immunity by oral routes. This data demonstrates that nanoparticles encapsulating antigen can be made to be more effective vaccines by the proper choice and engineering of recognition elements into the surface. By derivatizing the nanoparticles with a simple immune modulator (LPS), the nanoparticles' ability to elicit an immune response was significantly enhanced. Addition of modules to enhance particle targeting, internalization, endosome escape, and extracellular protection will increase the degree to which these elements can further enhance their efficacy as vaccine vehicles.

Example 3

Endosome Disruption Enhances Antigen-Presentation by Dendritic Cells

Materials and Methods:

Particles prepared using the same preparation discussed in Example 2 with 100 µl of endoporter added to the emulsion at a concentration of 1 mg/ml.

Results:

Many pathogens make use of the acidic pH environment of endosomes and lysosomes to penetrate out from the confines of endocytic organelles into the cytosol. Some, in fact, do this by secreting pore-forming peptides that are low pH activated. Endoporter is a commercially available synthetic peptide that accomplishes this function (Summerton, *Ann. N.Y. Acad. Sci.*, 1058:1-14 (2005)).

Figure 3:
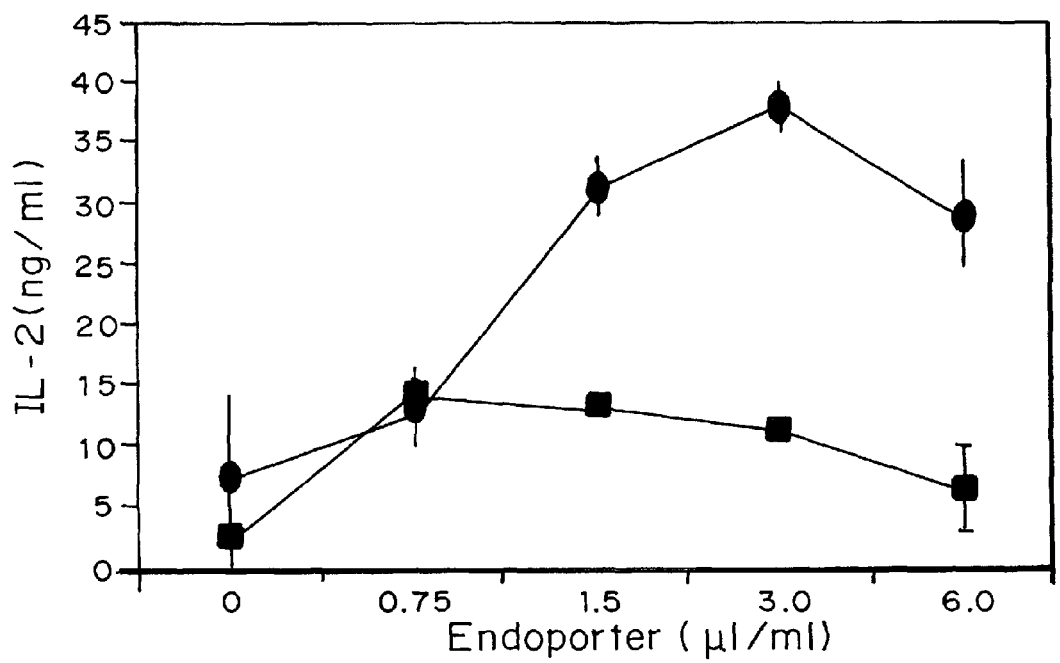
FIG. 3 is a graph showing release of IL-2 (ng/ml) by CD8 (OT-1) (-•-) and CD4 (OT-II) (-■-) positive T-cells as a function of the concentration of Endoporter (μl/ml) incubated with mouse bone marrow-derived dendritic cells. This graph demonstrates that inclusion of increasing concentrations of Endoporter enhanced cross presentation of antigen to MHC class I-restricted CD8 T-cells, while presentation to MHC class II-restricted CD4 T-cells was not diminished.

Mouse bone marrow-derived dendritic cells were incubated with soluble ovalbumin (0.1 mg/ml), a concentration that only inefficiently elicits antigen presentation to CD8 T cells. Inclusion of increasing concentrations of endoporter enhances cross presentation by 10-100-fold (depending on background) to the MHC class I-restricted, ovalbumin-specific CD8 T cell OT-I (as assayed by IL-2 release, (FIG. 3)). Importantly, presentation to MHC class II-restricted CD4 T cells (OT-II) was not diminished, even after endosome disruption (FIG. 3). Similar results were obtained when the ovalbumin was targeted to the dendritic cells by conjugation to anti-DEC-205 antibody. The results of these experiments demonstrate the efficacy of Endoporter in enhancing the presentation of exogenous antigens on MHC class I molecules to CD8 T cells, presumably by enhancing their penetration into the cytosol following endosomal disruption. Thus, endoporter significantly enhances a highly inefficient but essential aspect of antigen presentation required for effective immunity and vaccination to pathogens.

Example 4

Surface Modification of Nanoparticles With Protective Coatings Decreases Particle Degradation and Antigen Release Materials and Methods:

Particles were prepared as in Example 2. After lyophilization, biotin-elastin was prepared by biotinylation with NHS-LC-biotin (Pierce Chemicals). NHS-LC-biotin was incubated with 10 mg of particles (room temperature, 1 hour) at a concentration of 20 mg/ml. Following incubation, particles were washed by centrifugation 3× with deionized water and freeze-dried for further use. Controlled release studies were performed at the indicated pH.

Figure 4:
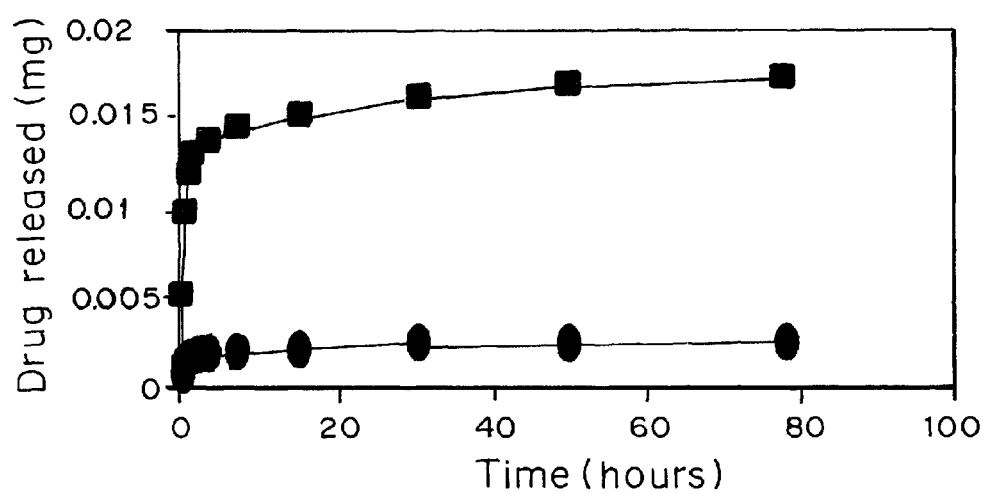
FIG. 4 is a graph demonstrating that nanoparticles conjugated to elastin (-•-) retain incorporated drug (mg) at low pH (pH=2) over time more readily than non-conjugated particles (-■-).

Results:

One advantage of antigen delivery using particles is the possibility of protecting the antigen against destruction in the GI tract following oral delivery. Elastin and poly(methacrylic) acid (PMAA) were conjugated to nanoparticles. As pH responsive polymers, both are in extended configurations at pH 7.4 and shrink rapidly (within seconds) upon exposure to lower pH environments (below pH 5 for elastin) and (below pH 5-6 for poly(methacrylic acid)). These data indicate that the addition of a pH responsive polypeptide or polymer to the surface of the nanoparticles can impart a protective effect to the particle affecting its degradation rate and antigen release (FIG. 4). The mechanism behind this protective ability may be due to the aggregation of the polymer at lower pH, restricting water entry and reducing the hydrolysis of the particle. Polymers such as PMAA in conjunction with poly(ethylene glycol) (PEG) have been used in past applications for enhancing the oral delivery of chemotherapeutic drugs, and thus there is good precedence for the use of these polymers as 'shielding' components in oral delivery (Blanchette and Peppas, *Ann. Biomed. Eng.*, 33(2):142-9 (2005); Blanchette and Peppas, *J. Biomed. Mater. Res. A*, 72(4):381-8 (2005)).

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims. Those skilled in the art will recognize, or be able to ascertain using no more than routine experimentation, many equivalents to the specific embodiments of the invention described herein. Such equivalents are intended to be encompassed by the following claims.

We claim:

1. A vaccine composition for inducing an immune response comprising
    an antigen selected from the group consisting of viral, bacterial, parasitic, allergen, toxoid, tumor-specific and tumor-associated antigens and
    an endosome-disrupting agent encapsulated in, attached on, or incorporated into a polymeric nanoparticle, wherein the endosome-disrupting agent is activated at the low pH of the endosome to enhance penetration into the cytosol of molecules in the endosome,
    the polymeric nanoparticle comprising on its surface a functional element comprising a dendritic cell or epithelial cell targeting molecule that specifically targets an internalizing surface molecule,
    the polymeric nanoparticle optionally comprising an adaptor element bound to or incorporated in the nanoparticle, wherein the functional element is bound to the nanoparticle by the adaptor element.

2. The composition of claim 1 wherein the adaptor element is coupled directly to the functional element by a covalent bond.

3. The composition of claim 1 wherein the adaptor element is conjugated to an affinity tag.

4. The composition of claim 3 wherein the adaptor element is coupled to the functional element by the non-covalent interaction of the affinity tag conjugated to the adaptor element and a complementary affinity tag conjugated to the functional element.

5. The composition of claim 1 further comprising a pH-sensitive or non-pH-sensitive molecule which protects the vaccine composition from hydrolysis and degradation in low pH environments.

6. The composition of claim 1 further comprising an adjuvant or immune modulator modulators.

7. The composition of claim 6 wherein the adjuvant or immune modulator is selected from the group consisting of a cytokine, an interleukin, an interferon, a macrophage colony stimulating factor, a tumor necrosis factor, and a member of the B7 family of co-stimulatory molecules.

8. The composition of claim 6 wherein the adjuvant or immune modulator is a glycolipid that is a stimulator of natural killer T cell-mediated immune responses.

9. The composition of claim 8 wherein the glycolipid is α-galactosylceramide.

10. The composition of claim 1 wherein the adaptor element comprises an element selected from the group consisting of a fatty acid, a hydrophobic or amphipathic peptide, and a hydrophobic polymer.

11. The composition of claim 3 wherein the affinity tag comprises avidin or streptavidin.

12. The composition of claim 1 wherein the targeting molecule is selected from the group consisting of a monoclonal or polyclonal antibody, a targeting molecule that targets the composition to a receptor on dendritic cells, a dendritic cell receptor, and a targeting molecule which targets the composition to a receptor on epithelial cells.

13. The composition of claim 5 further comprising molecules which protect the composition from hydrolysis and degradation in low-pH environments selected from the group consisting of elastin, poly(methacrylic acid), and poly(ethylene) glycol.

14. The composition of claim 1 further comprising a contrast agent, a fluorescent tag, or a radionuclide.

15. The composition of claim 1 further comprising a pharmaceutically acceptable excipient suitable for enteral administration.

16. The composition of claim 1 further comprising a pharmaceutically acceptable excipient suitable for parenteral administration.

17. A method for inducing an immune response to an antigen comprising administering to a subject in need an effective amount of the composition of claim 1.

18. The composition of claim 1 wherein the endosomal disruption agent is endoporter.

* * * * *